US005637657A

United States Patent [19]

Anton

[11] Patent Number: 5,637,657
[45] Date of Patent: Jun. 10, 1997

[54] SURFACE COATING COMPOSITIONS CONTAINING FLUOROALKYL ESTERS OF UNSATURATED FATTY ACIDS

[75] Inventor: Douglas R. Anton, Wilmington, Del.

[73] Assignee: E. I. Du Pont de Nemours and Company, Wilmington, Del.

[21] Appl. No.: 529,899

[22] Filed: Sep. 18, 1995

[51] Int. Cl.$^6$ ............... C08L 75/04; C08L 67/08; C08K 5/101; C08K 5/435
[52] U.S. Cl. ............... 525/445; 525/455; 525/454; 524/168; 524/316
[58] Field of Search ............... 524/168, 316; 525/445, 454

[56] References Cited

U.S. PATENT DOCUMENTS

| | | | |
|---|---|---|---|
| 3,378,609 | 4/1968 | Fasick et al. | 260/890 |
| 3,462,296 | 8/1969 | Raynolds et al. | 117/161 |
| 3,491,169 | 1/1970 | Raynolds et al. | 260/900 |
| 3,923,715 | 12/1975 | Dettre et al. | 260/29.6 |
| 4,539,006 | 9/1985 | Langford | 427/389 |
| 4,595,518 | 6/1986 | Raynolds et al. | 252/8.6 |
| 4,958,039 | 9/1990 | Pechhold | 556/421 |

FOREIGN PATENT DOCUMENTS

| | | |
|---|---|---|
| 2821495 | 11/1979 | Germany . |
| 3-167158 | 7/1991 | Japan . |
| 03167158-A | 7/1991 | Japan . |

OTHER PUBLICATIONS

Derwent Abstract of JP 50–047912.

*Primary Examiner*—David Buttner
*Attorney, Agent, or Firm*—George A. Frank; Nancy S. Mayer

[57] ABSTRACT

Perfluoroalkenoate esters containing at least two double bonds and coasting compositions, having durable advancing and receding hexadecane contact angles, containing such esters with alkyd or urethane resins are provided.

5 Claims, No Drawings

SURFACE COATING COMPOSITIONS CONTAINING FLUOROALKYL ESTERS OF UNSATURATED FATTY ACIDS

FIELD OF THE INVENTION

This invention relates to novel coating compositions containing fluoroalkyl esters of unsaturated aliphatic acids that provide durable oil- and water-repellent surfaces to the cured coating, and the cured coatings derived from such compositions.

BACKGROUND OF THE INVENTION

Conventional air-cure alkyd coatings utilize, as the binder or film-forming component, a curing or drying alkyd resin. By the term "alkyd coating", as used hereinafter, is meant a conventional liquid coating based on alkyd resins, typically a paint, clear coating, or stain. The alkyd resins are complex branched and cross-linked polyesters containing unsaturated aliphatic acid residues. The methods for preparing alkyd resins and formulating alkyd coatings from them are well known and are described in Surface Coatings Vol. I, Raw Materials and Their Usage (Chapman and Hall, New York N.Y., Second Edition, 1984).

Drying oils are liquid vegetable or synthetic oils such as linseed oil, soybean oil, safflower oil, and dehydrated castor oil. Linseed oil, a typical example of drying oils, is obtained from seeds of the common flax plant (Linum usitatissimum) and contains, inter alia, esters of glycerol with such unsaturated aliphatic acids as linolenic acid, linoleic acid and oleic acid.

Drying oils, and alkyd resins containing the unsaturated aliphatic acids derived from drying oils, spontaneously polymerize in the presence of air to yield a solid protective film. The polymerization is termed "drying" or "curing" and occurs as a result of autoxidation of the unsaturated carbon-carbon bonds in the aliphatic acid component of the oil by atmospheric oxygen. When applied to a surface as a thin liquid layer of formulated alkyd coating, the cured films that form are relatively hard, non-melting, and substantially insoluble in many organic solvents that act as solvents or thinners for the unoxidized alkyd resin or drying oil. Hereinafter the term "cured" is used to describe the autoxidized dried coating. Such drying oils have been used for centuries as raw materials for oil-based coatings and are described widely in the literature, e.g., in Surface Coatings Vol. I.

Conventional alkyd coatings use a prepolymer such as a drying oil alkyd resin as the film forming component in the cured alkyd coating. While these hydrocarbon polymers can give reasonable water repellency, they have little or no oil repellency. This lack of oil repellency can lead to the problem of staining by oily stains and are thus susceptible to soiling. In particular they have no resistance to wetting by oils, as demonstrated by their very low hexadecane contact angles.

Another conventional coating is the Type I urethane coating. Urethane coatings are classified by ASTM D-1 into five categories. Type I urethane coatings contain a pre-reacted autoxidizable binder as described in Surface Coatings Vol. I, previously cited. Type I urethane resins (binders), also termed urethane oils, oil-modified polyurethanes, or urethane alkyds, are the largest volume category of polyurethane coatings. By the term "urethane coating", as used hereinafter, is meant a conventional liquid coating based on Type I urethane resins, typically a paint, clear coating, or stain. Urethane coatings typically contain the reaction product of a polyisocyanate, usually toluene diisocyanate, and a polyhydric alcohol ester of drying oil acids. The cured coating is formed by air oxidation and polymerization of the unsaturated drying oil residue in the binder.

Urethane coatings give cured coatings with many desirable properties, but the cured coatings have little or no oil repellency as demonstrated by their very low hexadecane contact angles.

Certain commercial materials are known which provide oil repellency to textile and carpet substrates, such as aqueous perfluoroalkyl emulsion polymers (Fasick et al., U.S. Pat. No. 3,378,609, Dettre et al., U.S. Pat. No. 3,923,715, Raynolds et al., U.S. Pat. No. 3,462,296, U.S. Pat. No. 3,491,169 and U.S. Pat. No. 4,595,518, and Pechhold, U.S. Pat. No. 4,958,039). The treated substrates have outstanding oil and water repellency, however, the emulsion fluoropolymers utilized are not compatible with alkyds and urethanes.

The use of fluoroalkyl alcohol esters of alkanoic acids generally as lubricating aids is well known. For instance, the perfluoroalkyl ethyl ester of stearic acid has been used for imparting lubricity and repellency to various plastics. Also, Nishihara et al., JP308469 (1989), disclose the preparation of aliphatic carboxylic acid esters of various fluorinated alcohols, which can contain double bonds in the acid portion, and their use as lubricants for ferromagnetic metal thin film-type magnetic recording media.

Adding perfluoroalkyl ethyl stearate, a non-curing ("non-drying") fluoroalkyl ethanol ester of a saturated vegetable oil, to alkyd or urethane coatings in suitable formulations, however, provides at best only temporary oil and water repellency because the fluorinated component migrates to the surface but is not chemically bound with the autoxidized polymer. Thus the oil repellency is not durable and is readily lost when the surface is washed or otherwise cleaned.

It would be highly desirable to be able to provide cost effective, durable oil repellency to drying oil, alkyd, and urethane coatings.

There is a need to have a fluorinated moiety present at the liquid/air interface after application of the coating and prior to curing that is chemically bound, such as by crosslinking, to the coating to provide durable surface oil repellency.

SUMMARY OF THE INVENTION

The coating composition of this invention contains:

A. a perfluoroalkyl alkenoate ester having the structure

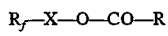

wherein
- O—CO—R is a $C_{10}$-$C_{24}$ alkenoic acid residue containing at least two double bonds;
- X is a divalent radical containing 1–20 atoms in the chain; and
- $R_f$ is a $C_1$-$C_{20}$ perfluoroalkyl group, and B. an alkyd or urethane resin wherein the coating composition contains 50–10,000 ppm by weight of fluorine of the non-volatile content of the coating composition and wherein a cured coating resulting from said coating composition has a durable advancing hexadecane contact angle of not less than 40° and a durable receding hexadecane contact angle of not less than 20°.

The perfluoroalkyl alkenoate esters of this invention have the structure:

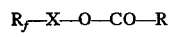

wherein

O—CO—R is a $C_{10}$–$C_{24}$ alkenoic acid residue containing at least two double bonds;

X is a divalent radical containing 1–20 atoms in the chain; and $R_f$ is a $C_1$–$C_{20}$ perfluoroalkyl group and $R_f$—X is selected from the group consisting of $R_f$—$SO_2$N(Et)—$CH_2CH_2$—, $R_f$—$SO_2$N(Me)—$CH_2CH_2$—, and $R_f$—$SO_2$N(Bu)—$CH_2CH_2$—.

DETAILED DESCRIPTION OF THE INVENTION

This invention comprises coating compositions containing perfluoroalkyl alkenoate esters having a structure:

$$R_f\text{—X—O—CO—R}$$

wherein —O—CO—R is a $C_{10}$–$C_{24}$ alkenoic acid residue, preferably a $C_{16}$–$C_{20}$ alkenoic acid residue, containing not less than two double bonds, preferably 2–3 double bonds. The alkenoic acids have iodine values equal to or greater than 120 and are exemplified by residues derived from linolenic, linoleic, eleostearic, and dehydrated castor oil acids.

In the above structure, X is a divalent radical containing from 1–20 atoms in the chain. The moiety $R_f$—X— is exemplified by:

$R_f$—$SO_2$N(Et)—$CH_2CH_2$—, $R_f$—$SO_2$N(Me)—$CH_2CH_2$—, $R_f$—$SO_2$N(Bu)—$CH_2CH_2$—, and $R_f$—$(CH_2)_m$— where m is 1–20, and $R_f$ is a $C_1$ to $C_{20}$ perfluoroalkyl group, either branched or straight chain.

By perfluoroalkyl is meant an alkyl radical containing the largest possible or a relatively large proportion of fluorine atoms in its structure and optionally containing ether oxygen atoms in the chain. The $R_f$ perfluoroalkyl groups are exemplified by perfluoroalkyl groups of the formula:

$$F(CF_2)_n\text{—}$$

where n is 2–20.

The iodine value is a characterization method for drying oils and drying oil acids, indicating the weight of iodine absorbed by the drying oil or drying oil acid expressed as a percentage (i.e., grams of iodine absorbed per 100 g test substance). Higher iodine values indicate more unsaturation; thus vegetable oils are classified in the coatings industry by the iodine value according to their film-forming ability. For instance, in Surface Coatings Vol. I, the following classification is made:

non-drying oils: iodine values <120, semi-drying oils: iodine values 120 to 150, and drying oils: iodine values >150.

An example of a non-drying oil is castor oil with an iodine value of about 85 and which contains about 90% esters of ricinoleic acid, a mono-unsaturated acid. An example of a semi-drying oil is soybean oil with an iodine value of about 130 and which contains mainly esters of linoleic acid, an alkanedienoic acid with two unsaturated bonds. An example of a drying oil is linseed oil with an iodine value of about 180 and which contains about 50% esters of linolenic acid, an alkanetrienoic acid with three unsaturated bonds. In general, coating compositions containing perfluoroalkyl esters having a relatively large proportion of alkanetrienoic acid residues are preferred.

The perfluoroalkyl unsaturated esters can be prepared by conventional methods for the synthesis of esters. Such methods include direct esterification of unsaturated acids with an $R_f$—X—OH alcohol, for instance perfluoroalkyl ethanol, or transesterification between an $R_f$—X—OH alcohol and the glycerol esters comprising a drying oil or the methyl esters of drying oil acids. The degree of incorporation of the $R_f$—X—OH alcohol can be maximized by using a molar excess of drying oil acid during esterification or of the drying oil during transesterification.

The requisite unsaturated acids can generally be obtained from natural vegetable oils. The acids can be obtained in the free acid form from the oils by saponification or hydrolysis, or in the methyl ester form by methanolysis. Different natural oils give different proportions of various unsaturated acids; such proportions being well known. The perfluoroalkyl unsaturated esters can generally be made from these naturally occurring mixtures of unsaturated acids, but they can also be made from purified single components.

The perfluoroalkyl ethanols can be prepared from the corresponding perfluoroalkyl ethyl iodides and are available commercially as ZONYL™BA Fluorotelomer Intermediate (a registered trademark of E. I. du Pont de Nemours and Company). ZONYL™BA contains alpha-fluoro-omega-(2-hydroxyethyl)-poly(difluoromethylene) in the form of a mixture of the components of the homologous series of the formula:

$$F(CF_2CF_2)_n(CH_2CH_2)OH,$$

containing therein:

for n=2, 1%–2% for n=3, 27%–34% for n=4, 29%–34% for n=5, 17%–21% for n=6, 6%–9% for n=7, 2%–5% for n=8, 1%–2%.

Other perfluoroalkyl alcohols can also be used in the present invention, such as 2-(N-ethyl perfluorooctane sulfonamido)ethanol, available commercially from 3M Company as FC-10™.

The perfluoroalkenoate esters are useful, among other applications, as components of coating compositions. By the term "coating composition", as used herein, is meant a liquid alkyd or urethane resin containing a fluorinated alkenoate ester, as applied to a substrate. By the term "cured coating" as used herein is meant the final decorative and/or protective film obtained after the volatile components of a coating composition have evaporated and the autoxidation process is substantially completed.

The coating compositions of this invention contain a mixture of an alkyd or urethane resin and sufficient perfluoroalkyl alkenoate ester of the above structure such that the coating composition contains 50–10,000 ppm by weight of fluorine of the non-volatile content of the composition and wherein the cured coating resulting from said composition has a durable advancing hexadecane contact angle of not less than 40° and a durable receding hexadecane contact angle of not less than 20°.

The contact angle formed between a surface and a drop of liquid is a measure of the wettability or repellency of the surface to the liquid. A wettable surface has low contact angles close to 0°; a repellent surface has higher contact angles. Thus the contact angle formed by an oily liquid such as hexadecane is widely used as a measure of the oil repellency of a surface.

Contact angles are measured by the Sessile Drop Method, which is described in A. W. Adamson, "The Physical Chemistry of Surfaces", Fifth Edition, Wiley & Sons, New York, 1990. Additional information on the equipment and procedure for measuring contact angles is provided by R. H. Dettre et al. in "Wettability", Ed. by J. C. Berg, Marcel Dekker, New York, 1993.

In the Sessile Drop Method, a Ramè-Hart optical bench is used to hold the substrate in the horizontal position. The contact angle is measured with a telescoping goniometer from the same manufacturer. A drop of test liquid is placed on a surface and the tangent is determined at the point of contact between the drop and the surface. An advancing angle is determined by increasing the size of the drop of liquid and a receding angle is determined by decreasing the size of the drop of liquid. The data are presented typically as advancing and receding contact angles.

The relationship between water and organic liquid contact angles, and cleanability and dirt retention of surfaces, is described in A. W. Adamson, above. In general, higher hexadecane contact angles are indicative that a surface has greater dirt and soil resistance and repellency, and easier cleanability of the surface.

By durable oil repellency and durable increased hexadecane contact angles are meant that the advantageous surface properties of cured coatings are retained following various simulations of surface cleaning. Two or more of the following five test procedures can be used to determine the durability of increased hexadecane contact angles.

Test Method 1—24 Hour Water Soak

Coated glass slides are immersed in water for 24 hours, removed and allowed to dry overnight under ambient conditions before measuring the contact angles as described above. Immediately following removal from water, contact angles are temporarily lowered, but recover as the coating dries if the improvement in contact angle is, in fact, durable.

Test Method 2—Commercial Glass Cleaner Wipe

Coated glass slides are sprayed with a commercial glass cleaner, wiped off with a soft paper towel, rinsed with water, and allowed to dry under ambient conditions before measuring the contact angles as described above. The commercial glass cleaner used in the Examples was Knights Glass and Stainless Steel Cleaner from Knights Marketing Corporation, Johnstown, N.Y., and contained 2-butoxyethanol, water, morpholine, ammonium hydroxide, and dioctyl sodium sulfosuccinate.

Test Method 3—Acetone Rinse

Coated glass slides are sprayed with acetone and allowed to dry under ambient conditions before measuring the contact angles as described above.

Test Method 4—Detergent Wash

Coated glass slides are immersed in a detergent solution for 15 minutes, rinsed with water, and allowed to dry overnight under ambient conditions before measuring the contact angles as described above. The detergent solution used in the Examples was a solution of 2 g DUPONOL™ WAQE (40% sodium lauryl sulfate in water) in 1 gallon of water, adjusted to pH 10 with trisodium phosphate.

Test Method 5—Isopropanol Wash

Coated glass slides are immersed in 20% by volume isopropanol solution for 15 minutes and allowed to dry overnight under ambient conditions before measuring the contact angles as described above.

The perfluoroalkyl unsaturated esters can be incorporated into conventional curable coating compositions in concentrations sufficient to afford a cured coating containing from approximately 50–10,000 ppm by weight of fluorine and preferably 150–5,000 ppm of fluorine and with durable hexadecane advancing and receding contact angles equal to or greater than 40° and 20°, respectively, and preferably equal to or greater than 60° and 40°, respectively. The perfluoroalkyl unsaturated esters can also be incorporated into the coating compositions of this invention directly as the reaction mixture in which they were synthesized, without isolation of the esters, provided the reaction solvents were chosen to be appropriate for the final coating composition. Examples of solvents compatible with the components of the coating compositions of this invention are mineral spirits, deodorized mineral spirits, Stoddard solvent, and other solvents compatible with alkyd and urethane coatings.

To prepare coating compositions containing an alkyd, the perfluoroalkyl unsaturated esters are mixed with an alkyd and stirred to give a homogeneous mixture. If the perfluoroalkyl unsaturated ester is added after isolation from the reaction mixture in which it was prepared, its dissolution can be facilitated by warming to 50° C. for about 30 minutes.

The preparation of coating compositions containing Type I urethanes and the perfluoroalkyl unsaturated esters can be accomplished as for alkyd-containing coating composition.

While the exact mechanism of the generation of the advantageous properties of the cured coatings (films) of this invention is not known, it is believed that the perfluoroalkyl alkenoate esters, when applied to a surface as part of the coating composition, migrate to the film surface before curing, become concentrated at the surface and chemically bound into the cured coating thus providing durable oil and water repellency to the cured coating.

The following Examples illustrate the preparation of the perfluoroalkyl alkenoate esters and the coating compositions of this invention in which they are utilized.

EXAMPLE 1

Preparation of Fluoroalkyl Ethanol Drying Oil Esters by Transesterification of Boiled Linseed Oil Linseed oil (boiled), 422 g, and 107 g of ZONYL™BA Fluorotelomer Intermediate (apparent MW 471) were added to a 3-necked round bottom flask equipped with a still head, mechanical stirrer and a nitrogen inlet. The mixture was heated to 60° C. to melt the alcohol and then purged with nitrogen for 20 minutes. The mixture was heated to 150° C. to form a solution and five drops of TYZOR™TPT Titanate (tetraisopropyl titanate, from the DuPont Company) were added. The mixture was heated to 210° C. and held for 2 hours with a slow nitrogen purge. The reaction mixture containing the fluoroalkyl alkenoate was then cooled to room temperature, forming a semi-solid mass.

EXAMPLE 2

Preparation of Fluoroalkyl Ethanol Drying Oil Esters by Esterification of Linseed Oil Fatty Acids A 500-ml, 4-necked, round bottom flask was equipped with a mechanical stirrer, nitrogen inlet, and a still head. The flask was charged with 112 g of Emery 644 Linseed oil fatty acid and 200 g of ZONYL™BA. Emery 644 consists of 54% linolenic acid, 20% oleic acid, 14% linoleic acid, 8% palmitic acid and 4% stearic acid. The flask was heated to 150° C. with an oil bath, with a slow nitrogen purge, and 5 drops of TYZOR™TPT were added. The temperature was increased to 175° C. and held for 4 hours. Several ml of water distilled from the mixture. Gas chromatography showed that >90% of the fluoroalkyl ethanol was reacted. The mixture containing the perfluoroalkyl alkenoate was cooled and bottled, yielding 298 g of a brown semisolid. A combustion analysis showed a fluorine concentration of 43.2%.

EXAMPLE 3

Esterification of Linoleic Acid with Mixed Perfluoroalkyl Ethanols

A 500-ml, 4-necked, round bottom flask was equipped with a mechanical stirrer, nitrogen inlet, and a still head. The flask was charged with 112 g of Emery 315 linoleic acid and 200 g of ZONYL™BA Fluorotelomer Intermediate. Emery 315 linoleic acid consists of 60% linolenic acid, 25% oleic acid, 9% linoleic acid, 4% palmitic acid, 1% myristic acid and 1% stearic acid. The flask was heated to 150° C. with an oil bath, with a slow nitrogen purge, and 5 drops of TYZOR™TPT were added. The temperature was increased to 175° C. and held for 4 and ½ hours. Several ml of water distilled from the mixture. Gas chromatography showed that most of the fluoroalkyl ethanol was reacted, and that there were higher boiling compounds present. The mixture was cooled and bottled, yielding 292 g of a brown semisolid. A combustion analysis showed a fluorine concentration of 43.1%. A gas chromatographic/mass spectroscopic analysis showed a mixture of the perfluoroalkyl ethyl fatty esters, identified by the parent ion peaks (624, 626, 724, 726) and the typical fatty acid splitting patterns. These results indicate the formation of the fluoroalkyl ethanol linoleic acid esters of this invention.

EXAMPLE 4

Esterification of Perfluorohexyl Ethanol with Linseed Oil Fatty Acids

A 50-ml 3-necked round bottom flask was equipped with a magnetic stirrer, still head, and a nitrogen inlet. It was charged with 6.8 g of Emery 644 Linseed Oil Fatty Acids, and 10.0 g of perfluorohexyl ethanol. It was then heated to 150° C. with an oil bath. Two drops of TYZOR™TPT were added and the temperature was increased to 175° C. and held for 5 hours. The mixture was then cooled to room temperature and bottled, yielding 15.8 g of a brown oil. Gas chromatographic/mass spectroscopic analysis showed the perfluorohexyl ethyl esters of oleic, linoleic, and linolenic acid (parent ions of 628, 626, 624), respectively. These results indicate the formation of the mixed linseed oil fatty acid esters of the mixed fluoroalkyl ethanols of this invention.

EXAMPLE 5

Preparation of FC-10™ Drying Oil Esters by Esterification of Linoleic Acid

FC-10™, 100 g, and 45 g of Emery 315 linoleic acid were added to a 250-ml 3-necked round bottom flask equipped with a nitrogen inlet, mechanical stirrer, and a still head. The reaction mixture was heated to 150° C. with an oil bath and 5 drops of TYZOR™TPT were added. The temperature was raised to 175° C. and held for four hours. The reaction mixture containing the perfluoroalkyl alkenoate was cooled to room temperature to yield 135 g of a waxy tan solid. Combustion analysis showed a fluorine concentration of 38.8%.

EXAMPLE 6

Preparation of Mixed Fluoroalkyl Ethanol Esters of Safflower Oil by Transesterification Safflower Oil (edible, 422 g) and ZONYL™BA Fluorotelomer Intermediate, 107 g, were combined in a 1 liter 3-necked round bottom flask equipped with a mechanical stirrer, nitrogen inlet and still head. The mixture was heated to 150° C. and five drops of TYZOR™TPT tetraisopropyl titanate were added. The temperature was then raised to 200° C. and held for two hours. The mixture was cooled to give a semisolid oil.

EXAMPLE 7

Preparation of the Fluoroalkyl Ethanol Drying Oil Ester of Linoleic Acid in Mineral Spirits A 1-liter round-bottom flask was equipped with a mechanical stirrer, nitrogen inlet, thermocouple and a Dean-Stark trap with a nitrogen bubbler. The flask was charged with 100 g of Emery 315 Linoleic acid, 160 g of ZONYL™BA, 0.2 g of p-toluenesulfonic acid, and 300 g of mineral spirits (CAS#8052-41-3). The mixture was heated to reflux (116°–130° C.), and water was collected in the Dean-Stark trap. The reaction was stopped when no more water was being distilled. A total of 8 ml of water was collected. The reaction mixture containing the perfluoroalkyl alkenoate was then cooled to give a dark solution/suspension. Gas chromatographic/mass spectroscopic analysis showed the presence of the unsaturated esters of the fluorinated alcohol. The suspended material dissolved on heating the suspension to approximately 60° C.

EXAMPLE 8

Preparation of a Coating Composition Based on Fluoroalkyl Ethanol Drying Oil Esters and Type I Urethane Coating Compositions A 0.5-ml aliquot of a reaction mixture containing the fluoroalkyl alkenoate prepared as in Example 1 was added to 20 ml of commercial polyurethane clearcoat [Designers Choice™ Polyurethane Clear Gloss Finish, from Enterprise Paint Co., containing mineral spirits, regular mineral spirits, and urethane modified alkyd resin, 51% solids] and warmed at 50° C. for 10 minutes to dissolve. Two microscope slides were coated, one with a control Type I urethane resin and the second with the composition of this invention. The slides were cured overnight. By eye, the static hexadecane contact angle of the control cured coating was 0° and the contact angle of the cured fluorinated coating was greater than 45°.

This observation shows that the coating composition of this invention containing perfluoroalkyl unsaturated esters and a urethane resin affords superior oil-repellency when compared to conventional cured resins.

EXAMPLE 9

Preparation of a Coating Composition Based on Fluoroalkyl Ethanol Drying Oil Esters and Type I Urethane Compositions A 1-g aliquot of a reaction mixture containing the fluoroalkyl alkenoate prepared as in Example 1 was added to 100 g of commercial polyurethane clearcoat (Designer's Choice™ Clear Polyurethane) and warmed to 50° C. for 10 minutes to dissolve. Several microscope slides (glass 1"×3") were coated with control urethane resin or with the composition of this invention by dipping and allowed to cure overnight. Separate slides were subjected to Test Methods 1 (water soak), 2 (glass cleaner wipe), and 3 (acetone rinse) and the hexadecane contact angles were measured. The results are shown in the following table:

| | | Hexadecane Contact Angle (°) | |
|---|---|---|---|
| | Sample | Advancing | Receding |
| 1. | Control coating, as prepared | 12 | 0 |
| 2. | Coating of this invention, as prepared | 74 | 51 |
| 3. | After Test Method 1 | 75 | 51 |
| 4. | After Test Method 2 | 80 | 59 |
| 5. | After Test Method 3 | 80 | 59 |

The data show that the cured coating of this invention has superior and durable oil-repellency.

EXAMPLE 10

Preparation of a Coating Composition Based on Fluoroalkyl Ethanol Drying Oil Esters and an Alkyd Coating Composition A 1-g aliquot of a reaction mixture containing the fluoroalkyl alkenoate prepared as in Example 1 was added to 100 g of Benjamin Moore Impervo™ Enamel Alkyd white paint and was warmed at 50° C. for 30 min. to dissolve. Wood panels were coated by brushing with either the control alkyd or with the composition of this invention and allowed to cure overnight. The cured coating showed excellent water and oil repellency by visual examination of the contact angles, relative to the cured control coating.

EXAMPLE 11

Preparation of a Coating Composition Based on Fluoroalkyl Ethanol Drying Oil Esters and a Type I Urethane Coating Composition A 0.25-g aliquot of a reaction mixture containing the fluoroalkyl alkenoate prepared as in Example 2 was added to 100 g of commercial polyurethane clearcoat (Designer's Choice™ Clear Polyurethane) and warmed to dissolve. Several microscope slides (glass 1"×3") were coated, with either the control polyurethane or with the composition of this invention, by dipping and allowed to cure overnight. Separate slides were subjected to Tests Methods 1 (water soak), 2 (glass cleaner wipe), and 3 (acetone rinse) and the hexadecane contact angles were measured. The results are shown in the following table:

| | | Hexadecane Contact Angle (°) | |
|---|---|---|---|
| | Sample | Advancing | Receding |
| 1. | Control coating, as prepared | 12 | 0 |
| 2. | Coating of this invention, as prepared | 80 | 58 |
| 3. | After Test Method 1 | 83 | 44 |
| 4. | After Test Method 2 | 74 | 51 |
| 5. | After Test Method 3 | 58 | 41 |

The data show that the cured coating of this invention has superior and durable oil-repellency.

EXAMPLE 12

Preparation of a Coating Composition Based on Fluoroalkyl Ethanol Esters and a Type I Urethane Resin Two portions of a commercial polyurethane (Designer's Choice™ Clear Polyurethane) were mixed with fluorine-containing esters. One contained 0.71 g of the safflower oil adduct prepared as in Example 6 in 100 g of polyurethane and the other 0.22 g of ZONYL™FTS Fluorotelomer Intermediate (the stearic acid ester of ZONYL™BA Fluorotelomer Intermediate, available from the DuPont Company) in polyurethane. The latter perfluoroalkyl ester is outside the scope of this invention. Each of these gave approximately 1000 ppm of fluorine in the coating composition. Several microscope slides (glass 1"×3") were coated with the coating composition of this invention and the polyurethane/ZONYL™FTS mixture by dipping and allowed to cure overnight. Slides were subjected to Test Methods 1 (water soak), 2 (glass cleaner wipe), and 3 (acetone rinse) and the hexadecane contact angles were measured. The results are shown in the following table:

| | Hexadecane Contact Angle (°) | | | |
|---|---|---|---|---|
| | with Safflower Oil Adduct | | with Stearate Adduct | |
| Sample | Advancing | Receding | Advancing | Receding |
| 1. Cured Coatings, as prepared | 76 | 43 | 63 | 5 |
| 2. After Test Method 1 | 79 | 59 | 52 | 0 |
| 3. After Test Method 2 | 80 | 58 | 53 | 6 |
| 4. After Test Method 3 | 80 | 57 | 0 | 0 |

The data show that the perfluoroalkyl unsaturated ester-based coatings of this invention provide durable surface oil repellency, while coatings based on perfluoroalkyl saturated ester provide neither as much oil repellency nor is the oil repellency durable.

EXAMPLE 13

Preparation of a Coating Composition Based on Fluoroalkyl Ethanol Esters and a Type I Urethane Resin Two samples of commercial polyurethane (Designer's Choice™ Clear Polyurethane) were mixed with fluorine-containing esters. One contained 0.25 g of the linoleic ester prepared as in Example 3 in 100 g of polyurethane and the other 0.25 g of ZONYL™FTS, in 100 g of polyurethane. Several microscope slides (glass 1"×3") were coated with the urethane resin coating composition of this invention or with the polyurethane and ZONYL™FTS Fluorotelomer Intermediate-based mixture, by dipping and allowed to cure overnight. Slides were subjected to Test Methods 4 (detergent wash) and 5 (isopropanol wash) and the hexadecane contact angles were measured. The results are shown in the following table:

| | Hexadecance Contact Angle (°) | | | |
|---|---|---|---|---|
| | with Linoleic Adduct | | with Stearate Adduct | |
| Sample | Advancing | Receding | Advancing | Receding |
| 1. Cured coatings, as prepared | 82 | 52 | 74 | 10 |
| 2. After Test Method 4 | 84 | 48 | 56 | 0 |
| 3. After Test Method 5 | 83 | 45 | 44 | 0 |

The data show that the perfluoroalkyl unsaturated ester-based coatings of this invention provide durable surface oil repellency, while coatings based on perfluoroalkyl saturated ester provide neither as much oil repellency nor is the oil repellency durable.

EXAMPLE 14

Preparation of a Coating Composition Based on Fluoroalkyl Ethanol Drying Oil Ester in Mineral Spirits and a Type I Urethane Coating Composition A warmed 0.5-ml aliquot of the reaction mixture containing the fluoroalkyl alkenoate prepared as in Example 7 was added to 100 g of Designer's Choice polyurethane. The solution was warmed at 50° C. for 20 minutes, and then a glass slide was coated with the mixture. After curing for two days, the coating had an advancing hexadecane contact angle of 78°, and a receding angle of 60°.

The results show that the perfluoroalkyl unsaturated esters of this invention can be prepared in a solvent compatible with commercial resins to provide durable surface oil repellency in the resulting cured coatings.

I claim:

1. A coating composition consisting essentially of
   A. a perfluoroalkyl alkenoate ester having the structure:

$R_f$—X—O—CO—R wherein
   O—CO—R is a $C_{10}$–$C_{24}$ alkenoic acid residue containing at least two double bonds;
   X is a divalent radical containing 1–20 atoms in the chain; and
   $R_f$ is a $C_1$–$C_{20}$ perfluoroalkyl group; and
   B. an alkyd or urethane resin wherein the coating composition contains 50–10,000 ppm by weight of fluorine of the non-volatile content of the coating composition and wherein a cured coating resulting from said coating composition has a durable advancing hexadecane contact angle of not less than 40° and a durable receding hexadecane contact angle of not less than 20°.

2. The coating composition of claim 1 wherein said $R_f$—X—moiety has the formula $F(CF_2CF_2)_n(CH_2CH_2)$— wherein n=2–8.

3. The coating composition of claim 1 wherein said O—CO—R moiety contains at least 50% linolenic acid grouping.

4. The composition of claim 1 wherein the urethane resin contains a pre-reacted autoxidizable binder.

5. A cured coating based on a coating composition consisting essentially of
   A. a perfluoroalkyl alkenoate ester having the structure:

$R_f$—X—O—CO—R wherein
   O—CO—R is a $C_{10}$–$C_{24}$ alkenoic acid residue containing at least two double bonds;
   X is a divalent radical containing 1–20 atoms in the chain; and
   $R_f$ is a $C_1$–$C_{20}$ perfluoroalkyl group; and
   B. an alkyd or urethane resin wherein the coating composition contains 50–10,000 ppm by weight of fluorine of the non-volatile content of the coating composition and wherein the cured coating resulting from the evaporation of the volatile components of said coating composition and the autoxidation of its components has a durable advancing hexadecane contact angle of not less than 40° and a durable receding hexadecane contact angle of not less than 20°.

* * * * *